US012599392B2

(12) United States Patent
Barthelmes et al.

(10) Patent No.: US 12,599,392 B2
(45) Date of Patent: Apr. 14, 2026

(54) MEDICAL INSTRUMENT WITH CONSISTENT SMOOTHNESS OF ACTION

(71) Applicant: Aesculap AG, Tuttlingen (DE)

(72) Inventors: Sven Barthelmes, Emmingen-Liptingen (DE); Holger Loesdau, Wurmlingen (DE); Christian Stark, Tuttlingen (DE); Markus Knecht, Penang (MY)

(73) Assignee: Aesculap AG, Tuttlingen (DE)

( * ) Notice: Subject to any disclaimer, the term of this patent is extended or adjusted under 35 U.S.C. 154(b) by 171 days.

(21) Appl. No.: 18/032,549

(22) PCT Filed: Oct. 18, 2021

(86) PCT No.: PCT/EP2021/078822
§ 371 (c)(1),
(2) Date: Apr. 18, 2023

(87) PCT Pub. No.: WO2022/084256
PCT Pub. Date: Apr. 28, 2022

(65) Prior Publication Data
US 2023/0380852 A1 Nov. 30, 2023

(30) Foreign Application Priority Data

Oct. 19, 2020 (DE) .................... 10 2020 127 497.1

(51) Int. Cl.
*A61B 17/28* (2006.01)
*A61B 90/00* (2016.01)
(52) U.S. Cl.
CPC .. *A61B 17/2816* (2013.01); *A61B 2090/0813* (2016.02)
(58) Field of Classification Search
CPC . A61B 17/28; A61B 17/2812; A61B 17/2816; A61B 17/29; A61B 17/3201;
(Continued)

(56) References Cited

U.S. PATENT DOCUMENTS

| | | | | |
|---|---|---|---|---|
| 3,459,187 A | | 8/1969 | Pallotta | |
| 5,514,147 A | * | 5/1996 | Hoskin | .............. A61B 17/2812 |
| | | | | 606/208 |

(Continued)

FOREIGN PATENT DOCUMENTS

| | | | | |
|---|---|---|---|---|
| CA | 3032489 A1 | * | 3/2018 | ............. A61B 17/28 |
| CN | 109496140 A | | 3/2019 | |

(Continued)

OTHER PUBLICATIONS

Search Report received in German Application No. 10 2020 127 497.1 dated Jul. 26, 2021, with translation, 15 pages.

(Continued)

*Primary Examiner* — Robert A Lynch
(74) *Attorney, Agent, or Firm* — Christopher A. Rothe; CM Law

(57) ABSTRACT

A medical instrument includes a first instrument branch having a first bearing portion with a first support surface, and includes a second instrument branch having a second bearing portion with a second support surface. The first support surface bears flat against the second support surface such that the first support surface can pivot in a sliding fashion so that the first instrument branch is pivotable relative to the second instrument branch about a pivot axis. The first bearing portion and/or the second bearing portion has, in the region of the pivot axis, a shoulder portion or a shoulder element with an end face that includes the associated support surface. The shoulder portion or shoulder element is stepped outwardly relative to the associated bearing portion in the direction of the pivot axis so that the associated support surface is stepped outwardly relative to the associated bearing portion.

19 Claims, 2 Drawing Sheets

(58) Field of Classification Search
CPC .. A61B 2017/00477; A61B 2017/0084; A61B 2017/00845; A61B 2017/2808; A61B 2017/2919; A61B 2017/2947; A61B 18/1442; A61B 18/1445; A61B 18/1447; A61B 2018/146; A61B 2090/0813; B25B 7/06; B25B 7/08; B26B 13/28
See application file for complete search history.

(56) References Cited

U.S. PATENT DOCUMENTS

| | | | |
|---|---|---|---|
| 7,326,229 | B2 | 2/2008 | Dworschak et al. |
| 10,448,991 | B2 | 10/2019 | Becker et al. |
| 2005/0120566 | A1 | 6/2005 | Dworschak et al. |
| 2012/0065466 | A1 | 3/2012 | Slater |
| 2019/0150965 | A1 | 5/2019 | Barthelmes et al. |
| 2020/0383695 | A1 | 12/2020 | Weisshaupt et al. |
| 2021/0275202 | A1 | 9/2021 | Gabele et al. |
| 2022/0151648 | A1 | 5/2022 | Barthelmes et al. |

FOREIGN PATENT DOCUMENTS

| | | | |
|---|---|---|---|
| DE | 10101425 | A1 | 7/2002 |
| DE | 10138393 | C1 | 3/2003 |
| DE | 10221321 | A1 | 11/2003 |
| DE | 102008058207 | A1 | 5/2010 |
| DE | 102016111892 | A1 | 1/2018 |
| DE | 102016116624 | A1 | 3/2018 |
| EP | 2594210 | A1 | 5/2013 |
| WO | 2018166989 | A1 | 9/2018 |
| WO | 2020182625 | A1 | 9/2020 |

OTHER PUBLICATIONS

Search Report received in International Application No. PCT/EP2021/078822 dated Jan. 25, 2022, with translation, 7 pages.
Written Opinion received in International Application No. PCT/EP2021/078822 dated Jan. 25, 2022, with translation, 12 pages.
Communication Pursuant to Art. 94(3) received in European Application No. 21 801 435.5 dated Apr. 10, 2024, with translation, 10 pages.
Office Action received in Chinese Application No. 202180070741.5 dated Feb. 2, 2026, with translation, 20 pages.

* cited by examiner

MEDICAL INSTRUMENT WITH CONSISTENT SMOOTHNESS OF ACTION

CROSS-REFERENCE TO RELATED APPLICATION(S)

This application is the United States national stage entry of International Application No. PCT/EP2021/078822, filed Oct. 18, 2021, and claims priority to German Application No. 10 2020 127 497.1, filed Oct. 19, 2020. The contents of International Application No. PCT/EP2021/078822 and German Application No. 10 2020 127 497.1 are incorporated by reference herein in their entireties.

FIELD

The present invention relates to a medical/medical-technical, in particular surgical, instrument with a first instrument branch, which has a first bearing portion with at least one first bearing surface/running surface/sliding surface, and with a second instrument branch, which has a second bearing portion with at least one second bearing surface/running surface/sliding surface, at/on which the first bearing surface rests/abuts/lies against each other in a flat, pivot-sliding manner, so that the first instrument branch is movable relative to the second instrument branch and is pivotable about a pivot axis.

BACKGROUND

Medical instruments, such as surgical clamps with two instrument branches that are pivotable to each other, usually have a bearing arrangement in the form of a push-through closure acting as a pivot joint, in which a male push-through part is accommodated in a female push-through box and is pivotable in a pivot-sliding manner into a closed, clamping position and into an open position on two directly abutting bearing surfaces of the two branches. These bearing surfaces, which lie directly on top of each other, are usually planar over the entire bearing portion or slope outward at a slight angle. The push-through closure has small clearances as well as sharp or distinctly angular inner corners or edges which, when the medical instrument is opened and closed, rub over the respective opposite, directly adjacent bearing surface as well as over the edges of this bearing surface. On the one hand, a length of the contacting edge changes over an opening movement or closing movement, and on the other hand, the clearances between the bearing surfaces are unequal or increasing. As a result, uneven action with an associated different smoothness of action occurs in the range of motion of the relative movement. In particular, depending on the relative orientation/opening position of the instrument branches to each other, a friction or respectively frictional force between the bearing portions of the instrument branches changes, resulting in uneven action. Such an effect of uneven action can be observed, for example, in surgical scissors, which require a higher closing force with increasing closing position.

U.S. Pat. No. 3,459,187 A, for example, discloses a medical instrument in the form of a surgical clamp with two instrument branches in push-through configuration which are pivotable relative to each other. In a pivot-joint region, a male push-through part protrudes through a female push-through box and rests against the inner walls of the latter over its entire surface. During an opening movement and closing movement, the male and female bearing portions slide off each other under friction. Accordingly, a smoothness of action changes when the instrument branches are pivotable positioned in relation to each other.

WO 2018/166 989 A1 discloses an additively manufactured surgical clamp with two instrument branches which are pivotable relative to each other. One instrument branch has a guide projection which rises in the direction of the other instrument branch and engages in a correspondingly formed arcuate recess in the other instrument branch for pivoting positioning of the instrument branch. Also, in this surgical clamp, a smoothness of action differs in the range of motion, in particular when the clamp is opened from the closed position. Component stability in the open state is also comparatively low and susceptible to breakage if handled incorrectly.

SUMMARY

It is therefore the object of the invention to avoid or at least reduce the disadvantages of the prior art and, in particular, to provide a medical instrument that maintains a particularly uniform smoothness of action throughout the entire range of motion or respectively in each relative orientation of the instrument branches to each other. Furthermore, manufacturing and production, in particular an assembly process, is to be simplified. Another object of the invention is to minimize production-related surface defects such as scratches on a visible bearing surface. In addition, cleanability or respectively sterilizability is to be improved.

Basically, the invention thus provides that the (at least one) first bearing surface and/or the (at least one) second bearing surface in the region of the pivot axis or respectively around the pivot axis is recessed outward/offset outward with respect to its (remaining) bearing portion in the direction of the pivot axis of the medical instrument and thus toward the second or respectively first bearing surface. By this configuration, a projection portion is formed, which specifically defines the bearing surface, in particular on one side as a whole, and forms a (small) gap between the (remaining) wall surfaces of the bearing portion facing each other via the elevation by the shoulder portion/elevation portion or the shoulder element/elevation element. Since, as a result, only the offset bearing surface around the pivot axis is in direct contact with the corresponding opposite bearing surface, the latter may be specially configured and, for example, be particularly well machined and prepared for pivot-sliding use. A particularly high surface quality of this bearing surface can be produced by local machining. Due to the gap created in the remaining part/portion of the bearing portions, the production-related different clearances are no longer relevant and without influence, so that an action or respectively a smoothness of action in the entire movement field is further harmonized or approximated to a uniform, constant action over the entire relative movement. The configuration with the offset portion or offset element thus ensures an even more uniform action, increases a component stability, and optimizes a capillary behavior during an electrochemical processing through clearances that remain constant along, in particular, the bearing portion. Due to the special design of the instrument, in which the bearing surface is offset outward relative to the associated bearing portion or respectively protrudes (outward) relative to the bearing portion toward the other instrument branch and forms the pivot-sliding contact surface toward the other instrument branch, this bearing surface can be specifically machined to achieve a particularly high surface quality locally (in particular relative to the remaining surface of the bearing portion). The limited and geometrically precisely defined pivot-sliding bearing surface enables and achieves simple and efficient manufacture of the medical instrument.

In particular, the shoulder portion or shoulder element may be heat treated in order to achieve a different property of the material of the shoulder portion or shoulder element, in particular of the bearing surface, compared to the remaining part of the medical instrument.

Also, in particular the shoulder portion or the shoulder element, in particular the bearing surface, may be surface treated, preferably surface hardened and/or nitrided and/or phosphated, in order to locally reduce, e.g., friction and wear. Preferably, only the shoulder portion or the shoulder element, in particular the bearing surface, is surface-treated (and the remaining part of the instrument is not), in order to achieve a cost-effective production with locally high surface quality.

In addition, in particular the shoulder portion or shoulder element, in particular the bearing surface, may be hardened and have a higher hardness than the rest of the bearing portion, in particular than the rest of the medical instrument.

Preferably, the shoulder portion or the shoulder element may also have a biocompatible coating forming the bearing surface, in particular with polymers, in particular fluoropolymers, and/or with PEEK and/or with titanium.

In particular, in the case where both the first bearing portion and the second bearing portion have a shoulder portion or shoulder element whose front faces each form the bearing surfaces, only these have to be subjected to special machining in order to ensure in particular a low roughness for a uniform pivoting movement. If both front faces are also planar, a uniform surface with only very slight unevenness can be achieved. Production with corresponding special machining of the bearing surfaces can be even simpler and more cost-effective, and the ergonomics of the instrument can be further improved.

Such a configuration brings the advantages of higher mechanical load-bearing capacity, process-reliable machine production, an increase in a degree of mechanization or automation in production, and concomitantly better cleaning properties. The slight increase in clearance also creates space for further structural adjustments, such as additional rounded edges. An optimized cleaning result is also achieved by the gap or respectively the clearance which is arranged between the opposite 'inner surfaces' of the bearing portions and which in particular remains the same. Electrochemical machining is also optimized.

According to the invention, therefore, the first bearing portion and/or the second bearing portion has, in the region of the pivot axis, a shoulder portion or a shoulder element with a front face comprising or forming the associated bearing surface, said shoulder portion or shoulder element being recessed outward/standing out/offset/protruding or projecting outward in the direction of a pivot axis of the medical instrument relative to the associated bearing portion, so that the associated, in particular entire, bearing surface is also offset outward relative to the associated bearing portion. In particular, at least the first bearing portion has, in the region of the pivot axis, at least one shoulder portion or a shoulder element with a front face comprising, in particular forming, the first bearing surface, said shoulder portion or shoulder element being offset outward relative to the first bearing portion in the direction of the pivot axis, so that the first bearing surface is offset outward relative to the first bearing portion toward the second bearing surface.

The term 'pivot-sliding' means that the two bearing surfaces slide on each other over their flat surface and perform a pivoting movement relative to each other about a pivot axis. This occurs, for example, when a first plane (wall) surface rests directly, for example horizontally, on a second plane (wall) surface and these two surfaces are rotated against each other so that they rest on each other in a pivot-sliding manner.

The front face is a side of the shoulder portion or shoulder element that projects toward the other bearing portion or respectively the other bearing surface in order to lie flat on the other bearing surface. At least part of the front face forms the bearing surface. In particular, the pivot axis is perpendicular to the front face. The front face therefore faces away from the bearing portion or respectively points away from it (outward).

The expression 'in the area of the pivot axis' defines that the shoulder portion or shoulder element is arranged in the area around the pivot axis, and thus in particular in a central, middle portion of the bearing portion. The lateral portions of the bearing portion (i.e. outside the area of the pivot axis), on the other hand, do not have a shoulder portion or shoulder element. The first and second bearing portions are spaced apart from each other and therefore do not serve as bearing surfaces.

The term 'offset' defines that there is an offset between the bearing surface and the rest of the bearing portion in the direction of the pivot axis. Similar to a plateau, platform or elevation, where the upper plateau/platform/elevation surface forms a surface offset from the ground, the bearing surface is offset with respect to a base surface of the bearing portion.

According to a further aspect of the invention, the first bearing surface and the second bearing surface are configured and correlated/coordinated with each other such that during sliding relative movement of the first instrument branch to the second instrument branch, an area size of a contact surface of the two bearing surfaces lying on top of each other is the same (size) in each relative orientation/relative position in order to maintain a smoothness of action uniformly in the entire range of movement of the relative movement. In contrast to the prior art, the technical configuration of the medical instrument and the bearing surfaces lying on top of each other does not change the surface area of the contact surface of the two bearing surfaces, i.e. the surface area of the two opposite bearing surfaces that lie directly on top of each other in the respective relative orientation, which results in a constant frictional force and, consequently, in a constant smoothness of action. Due to such a configuration with corresponding matching of the bearing surfaces, the contact surface between the bearing surfaces is the same in every position. This ensures uniform action along the entire movement field and increases component stability. Due to the constant contact surface (support surface), the same frictional forces prevail in every (opening) position. The term relative orientation in the entire movement field refers to any possible relative positioning or position of the two instrument branches between a closing position and a maximum opening position.

In particular, at least the first bearing portion has at least one offset first bearing surface, which has a consistently large contact surface with the second bearing surface regardless of the opening position or relative orientation. This results in a particularly uniform smoothness of action over the entire field of movement of the medical instrument, which also has good cleaning properties and is easy to manufacture.

According to a preferred embodiment, the entire first bearing surface(s) may fully rest on the second bearing surface(s) in any relative orientation. Since the (at least one) first bearing surface is always fully supported on the (at least one) second bearing surface, the size of a contact surface does not change and the smoothness of action remains the same. As a result, the first bearing surface thus does not come into a field of view of a user. In other words, at least the first bearing portion has such a first bearing surface, which has a contact surface of constant size regardless of the opening position of the two branches relative to the second bearing surface. In particular, the entire first bearing surface rests on the entire second bearing surface in any relative orientation. In particular, the first and/or second bearing surfaces are limited to the non-visible part of the 'closing surface' or contact surface and do not come into a field of view in any (relative) position of the instrument branches.

Preferably, the first bearing surface and/or the second bearing surface may be planar, i.e. lying in one plane. This makes for particularly simple manufacture and good pivot-sliding properties.

According to a further preferred embodiment, the first bearing surface and/or the second bearing surface may be formed rotationally symmetrical, in particular circular or annular with a circular outer diameter, which in particular rests in its entire surface on the respective other bearing surface in each relative orientation of the entire range of motion and forms the contact surface. In particular, due to the circular configuration of the bearing surface, which is arranged concentrically around the pivot axis, the circular circumferential edge is tangential to a direction of movement during a pivoting movement, so that an influence, in particular a frictional influence, by the circumferential edge is minimized. Thus, the same frictional forces exist in each relative orientation and, in particular, no component edge touches the bearing surface. The opposite, adjacent bearing surface can then be approximately flat, in particular planar, over the entire bearing portion. Due to the circular configuration of one bearing surface (on at least one side), a frictional force and thus a smoothness of action are kept even.

In particular, the at least one first and/or at least one second bearing surface has a continuous surface, so that a contact surface also forms a continuous surface. In this way, additional frictional influences are minimized and in particular a size of the respective bearing surface is maximized in order to increase component stability.

According to one aspect of the invention, the first bearing portion and/or the second bearing portion may comprise a stepped portion/pedestal, in particular a cylindrical or hollow-cylindrical stepped portion/pedestal, having a planar front face forming the bearing surface as a shoulder portion or shoulder element. In particular, a ratio of an outer diameter of the cylindrical or hollow-cylindrical stepped portion/pedestal to a height of the stepped portion (in the direction of the pivot axis starting from the base of the stepped portion) and thus to the associated bearing surface is between 10:1 and 200:1, preferably between 50:1 and 100:1. Similar to a flat, planar plateau, the planar front face forms the bearing surface. Preferably, a clearance hole may be concentrically formed in the stepped portion.

According to one embodiment, the shoulder portion may be formed integrally on/with the associated bearing portion, in particular with the associated instrument branch. Integral manufacturing of this kind avoids additional crevices and gaps, which further improves cleaning properties and increases component stability. A manufacturing process is also simplified, since separate production and assembly are not required.

According to a further preferred embodiment, the medical instrument may have a push-through configuration/a push-through closure, in which the first bearing portion is a male bearing portion in the form of a push-through part and the second bearing portion is a female bearing portion in the form of a push-through box having a passage opening, in which the male bearing portion engages through the passage opening of the female bearing portion and pivotally slides against two averted bearing surfaces/support surfaces/abutment surfaces of the male bearing portion against two facing bearing surfaces of the female bearing portion. A push-through configuration is particularly stable and easy to manufacture as well as to clean or respectively sterilize.

Preferably, the male bearing portion may have two circular or annular stepped portions facing away from each other, coaxially arranged with respect to each other and with a planar front face, which form the two first (male) bearing surfaces of the male bearing portion facing away from each other. Such a configuration on both sides of the male portion contributes to a uniform smoothness of action on both sides and at the same time increases a component stability and a cleaning property.

According to one embodiment, the bearing surfaces are configured and matched to each other in such a way that always only one surface of the other bearing surface rests without edges on one bearing surface. In other words, in particular the bearing surface or respectively the contact surface are not interrupted by edges in any relative orientation. In yet other words, no component edge touches the bearing surface in any relative orientation. This makes smoothness of action even more uniform.

According to one aspect of the invention, the medical instrument may be a surgical clamp or surgical forceps. In a surgical clamp or forceps, a consistent smoothness of action is of particular interest.

According to a further embodiment, the first bearing surface and/or the second bearing surface may have a rounded edge/chamfer around the circumference/on the outside/on the contour. This increases component stability, simplifies a manufacturing process and ensures a constant frictional force at the circumference and thus a constant action.

Preferably, a height of the shoulder portion or of the shoulder element starting from the foot of the shoulder portion or of the shoulder element in the direction of the pivot axis may be a minimum of 0.1 mm and/or a maximum of 1 mm, particularly preferably a minimum of 0.3 mm and/or a maximum of 0.6 mm. Alternatively or additionally, a height of a gap or a clearance between the first bearing portion and the second bearing portion in the direction of the pivot axis 11 may be a minimum of 0.1 mm and/or a maximum of 1 mm, particularly preferably a minimum of 0.3 mm and/or a maximum of 0.6 mm.

In particular, the shoulder portion of the first bearing portion is identical to the shoulder portion of the second bearing portion. Thus, a symmetrical structure is provided and also manufacturing can be adjusted to only one embodiment of the shoulder portion.

Preferably, a roughness/surface roughness Ra of the first bearing surface and/or of the second bearing surface may be less than preferably less than Ra 0.4 μm.

Preferably, the first and/or second bearing surface may have an area of at least 0.5 cm$^2$ and/or at most 5 cm$^2$.

Preferably, a diameter of a through bore coaxial with the pivot axis can be no more than 25% of the outer diameter of the shoulder portion or of the shoulder element. This ensures a sufficient support surface and contact surface of the two bearing surfaces.

In particular, the first bearing surface and/or the second bearing surface may have a surface treatment or coating to ensure particularly good bearing/running properties. For example, the shoulder portion and thus also the bearing surface may have a special structure, such as a martensite, in order to achieve high strength with good forming properties. The bearing surface may also have a low-friction coating.

BRIEF DESCRIPTION OF THE DRAWINGS

The invention is explained in more detail below with reference to a preferred embodiment with the aid of figures. The following is shown.

The figures are schematic in nature and are intended only to aid understanding of the invention. Identical elements are marked with the same reference signs.

DETAILED DESCRIPTION

Figure 1:
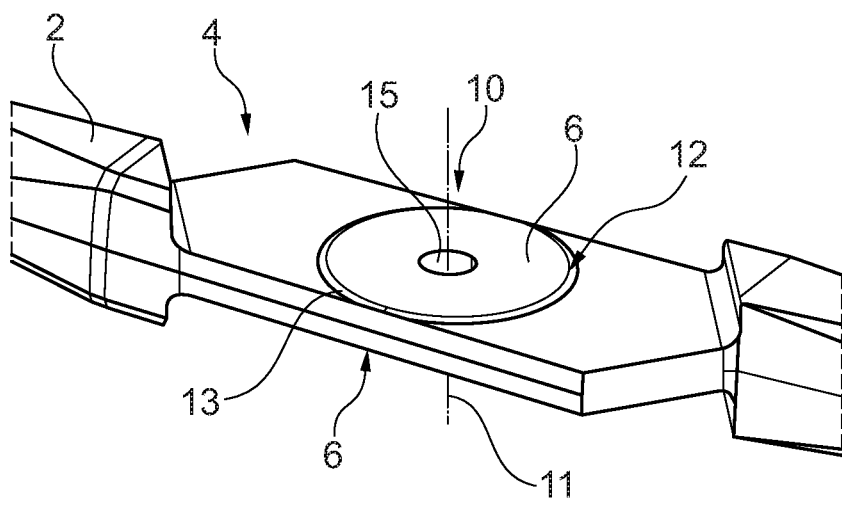
FIG. 1 shows a partial perspective view of a male bearing portion of a medical instrument according to the invention of a preferred embodiment.
Figure 2:
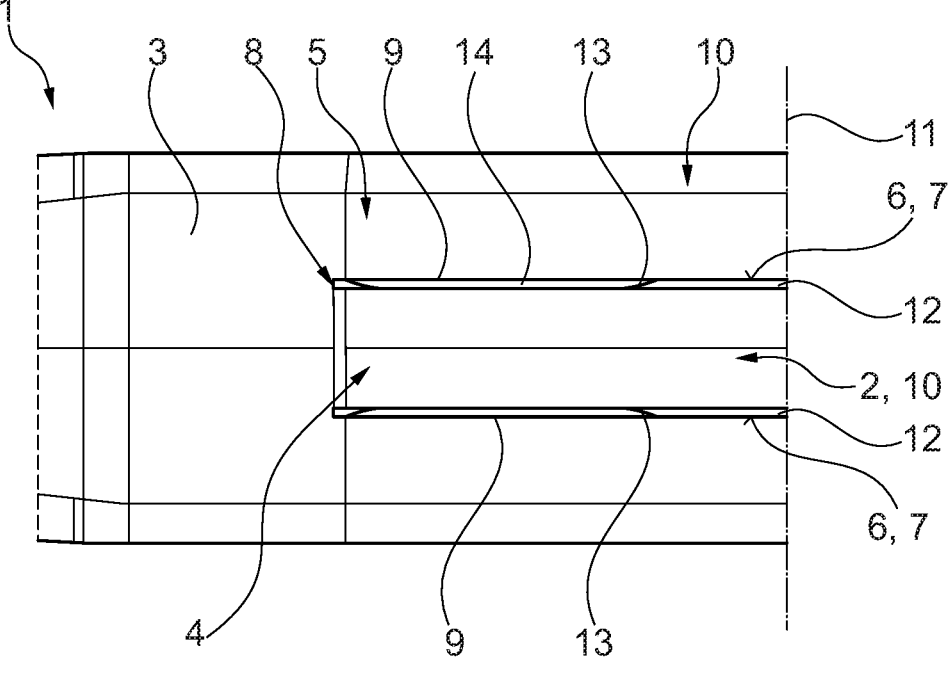
FIG. 2 shows a partial top view of the bearing portion of the medical instrument according to the preferred embodiment.
Figures 3, 4, 5, 6:
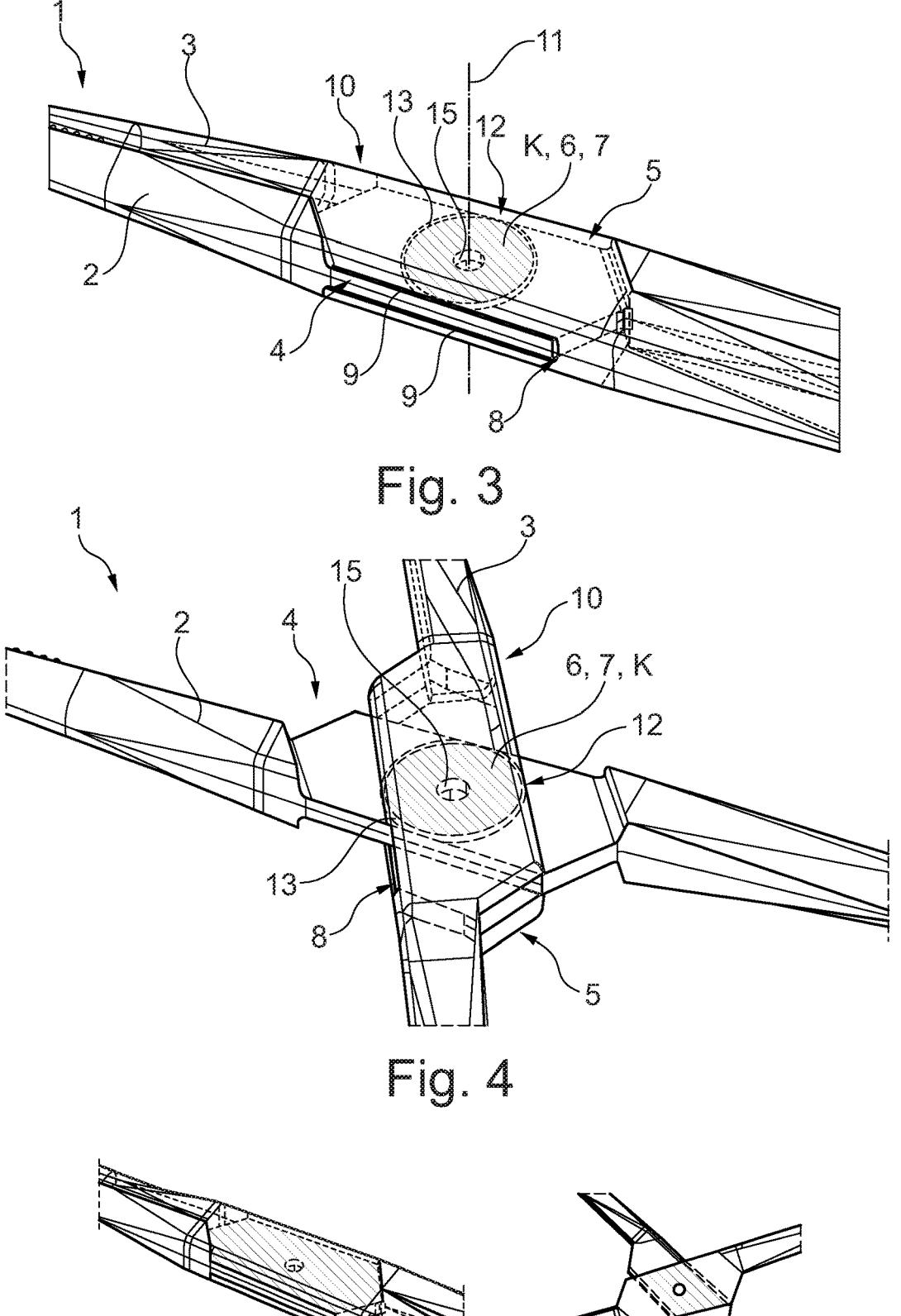
FIG. 3 shows a partial perspective view of the medical instrument of FIGS. 1 and 2 in an assembled state of use with closed instrument branches.
FIG. 4 shows a partial perspective view of the medical instrument of FIG. 3, in which the instrument branches are swung apart.
FIGS. 5 and 6 show a push-through closure according to the prior art.

FIGS. 1 to 4 show a medical instrument 1 of a preferred embodiment in the form of a surgical clamp. FIG. 1 shows its male instrument branch 2 and FIGS. 2 to 4 show both the male instrument branch 2 and a female instrument branch 3 pivotable to it in the assembled, ready-to-use state of the instrument 1, in which the instrument 1 is usable for a surgical procedure and the male and female instrument branches 2, 3 can no longer be separated from each other.

The male instrument branch 2 has a rear/end-side proximal gripping portion/handle portion (not shown here), a front-side distal clamping portion (not shown here), and a male bearing portion arranged between them in the form of a push-through part 4 in the form of a parallelepiped. Similarly, the female instrument branch 3 has a gripping portion (not shown), a clamping portion (not shown) and a female bearing portion arranged therebetween in the form of a female push-through box 5. For bearing purposes, the female push-through box 5 has a push-through/passage opening 8 in which two facing or opposite, parallel, plane side surfaces 9 are formed into which the male push-through part 4 engages.

As shown in FIGS. 2 to 4, the two instrument branches 2, 3 lie flat in a pivotable manner with the bearing portions 4, 5 via a male bearing surface/running surface 6, which is formed on the side of the male bearing portion 4, and a female bearing surface/running surface 7, which is formed on the side of the female bearing portion, so that the male instrument branch 2 is pivotable relative to the female instrument branch 3 between relative positions of a maximum opening position, in which the clamp is completely open, and a closing position, in which the two front-side clamping portions lie on top of each other in a clamped manner.

In contrast to the prior art, the male bearing portion 4 shown enlarged in FIG. 1 has a circular, cylindrical or ring-shaped stepped portion/pedestal 12 as a shoulder portion in a central bearing subregion 10 facing away on both sides and extending in the direction of a pivot axis 11. Both stepped portions 12 facing away from each other are coaxial with each other and each have a plane surface of the same size on the front side, which in each case form the male bearing surface 6 and face away from each other and are parallel to each other. These two stepped portions 12 around the pivot axis 11 or concentric to it with the bearing surface 6 offset have the effect that only this part of the (front side) surface of the male push-through part 4 comes into contact as bearing surface 6 with the respective female bearing surface 7 (see FIG. 2). The plane bearing surface 6 is parallel to and spaced apart from the remaining plane surface of the bearing portion 4. A uniform smoothness of action is achieved by the area of the bearing surface 6 that is offset in a defined manner from the remaining area of the bearing portion 4 and is in contact with the female bearing surface 7.

Since, as shown in FIGS. 3 and 4, the round male bearing surface 6 is always in full contact with the female bearing surface 7 in every relative position or relative orientation of the two instrument branches 2, 3, a (size of a) contact surface K between the male bearing surface 6 and the female bearing surface 7 is always the same. As a result, an action is also equally pronounced in the entire range of motion or respectively in each relative orientation of the two instrument branches 2, 3 to each other and a smoothness of action is uniformly maintained. In addition, the bearing surfaces 6, 7 or respectively the contact surface K are never interrupted by edges in any relative orientation, which also ensures uniform action. This results from the constant contact surface K and in particular the round shape of the offset male bearing surface 6 with circular outer contour. The male bearing surface 6 lies completely on the female bearing surface 7 in every relative orientation and never comes into view.

It should be noted at this point that in the case of the parallel side surfaces/side walls 9 of the push-through box 5, only a central or middle surface part of the side surfaces 9 comes into contact with the circular male bearing surfaces 6 and only these central surface parts rest on the male bearing surface 6 or respectively lie against each other for a pivot-sliding movement. As a result, of course, only these surface parts form the female bearing surfaces 7.

In order to further improve a pivoting movement, an action as well as cleanability, the male bearing surfaces 6 at the stepped portion 12 have a rounded edge/chamfer 13 circumferentially at their circular circumference or respectively their radial outer circumferential edge. Furthermore, the rounded stepped portion 12 extends (in diameter direction, i.e. perpendicular to the direction of the pivot axis) up to the (outer) edge or respectively along an entire width of the push-through part in order to be flush therewith and to form a maximum possible circular support surface or male bearing surface 6.

The two stepped portions 12 are formed integrally with the male instrument branch 2 and have only a very small height in the direction of the pivot axis 11, in order to only slightly increase a clearance or respectively a gap 14 between the remaining part of the push-through part 4 to the push-through box 5. In particular, a height of the stepped portion 12 and thus of the gap 14 may be at least 1% and/or at most 10% of a thickness of the push-through part 4 in the direction of the pivot axis 11. In particular, the stepped portion 12 may be additively manufactured as shoulder portions on the push-through part 4 of the male instrument branch 2.

For a positionally fixed, pivoting bearing around the pivot axis 11, the male instrument branch 2 has a clearance hole/push-through axis/through bore 15 in the direction of the pivot axis 11 in the center of the two stepped portions 12 or respectively coaxial to them. In combination with complementary, preferably cylindrical, facing projections (not shown) on the parallel side surfaces 9 centered on the female bearing surface 7, the male bearing portion is thus pivotably mounted by engaging in the clearance hole 15.

In particular, the male bearing surfaces 6 have a predetermined roughness in order to (slightly) increase or decrease a smoothness of action. The roughness can thus be used to fine-tune the smoothness of action. Alternatively or additionally, the female bearing surface 7 may also have a predetermined roughness.

FIGS. 5 and 6 show a push-through closure according to the prior art for comparison. In these, the bearing surface is not offset and an area size of a contact surface of a male and female bearing surface changes during a pivoting movement. As a result, the smoothness of action also changes. Similarly, edges of both a male and a female bearing portion drag over corresponding bearing surfaces, which also changes a smoothness of action.

In contrast to the prior art, as explained above, in the instrument 1 according to the invention as shown in FIGS. 1 to 4, due to the stepped portion 12 with the circular, offset bearing surface 6, an area size of the contact surface K always remains the same for a uniform smoothness of action and no edges lie on the bearing surfaces 6, 7.

The invention claimed is:

1. A medical instrument comprising:
a first instrument branch comprising a first bearing portion with a first bearing surface, the first bearing surface consisting of a first planar surface; and
a second instrument branch comprising a second bearing portion with a second bearing surface, the second bearing surface consisting of a second planar surface, the first bearing surface resting on the second bearing surface in a pivot-sliding manner, so that the first instrument branch is pivotable about a pivot axis relative to the second instrument branch,
the first bearing surface and the second bearing surface forming an interface where the first bearing surface and the second bearing surface contact one another and slide along one another under a frictional resistance during sliding pivot movement of the first instrument branch relative to the second instrument branch,
the first bearing portion comprising a first stepped portion that is surrounded by a first shoulder portion such that the first bearing surface projects from the first instrument branch,
the first shoulder portion defining a rounded sidewall consisting of a continuously rounded surface devoid of inside corners or gaps,
the interface consisting of a continuous planar area devoid of any void space between the first bearing surface and the second bearing surface, the continuous planar area having a fixed boundary and a fixed orientation relative to the pivot axis that remain constant during sliding pivot movement of the first instrument branch relative to the second instrument branch, and the first bearing portion comprising two circular pedestals facing away from each other on opposite sides of the first instrument branch, the two circular pedestals being coaxially arranged with respect to each other and comprising planar front faces that collectively define the first bearing surface.

2. The medical instrument according to claim 1, wherein the interface has a surface area that remains constant during sliding pivot movement of the first instrument branch relative to the second instrument branch, so that the frictional resistance remains constant throughout an entire range of sliding pivot movement of the first instrument branch relative to the second instrument branch, thereby maintaining a uniform smoothness of action during said entire range of sliding pivot movement.

3. The medical instrument according to claim 1, wherein the first bearing surface rests entirely on the second bearing surface and/or the second bearing surface rests entirely on the first bearing surface in each relative orientation.

4. The medical instrument according to claim 1, wherein the first stepped portion comprises a pedestal bounded by the rounded sidewall.

5. The medical instrument according to claim 4, wherein the pedestal is a cylindrical pedestal.

6. The medical instrument according to claim 1, wherein the first stepped portion is integrally formed on the first instrument branch.

7. The medical instrument according to claim 1, wherein the medical instrument has a push-through configuration in which the first bearing portion comprises a push-through part, and the second bearing portion comprises a push-through box having a passage opening, in which the first bearing portion engages through the passage opening and pivotably slides against the second bearing portion.

8. The medical instrument according to claim 1, wherein the medical instrument is a surgical clamp or surgical forceps.

9. The medical instrument according to claim 1, wherein the first bearing surface and/or the second bearing surface has a rounded edge around a circumference.

10. The medical instrument according to claim 1, wherein the first stepped portion comprises a height in a direction of the pivot axis of between 0.1 mm to 1 mm.

11. The medical instrument according to claim 1, wherein the first bearing portion and the second bearing portion define a gap having a height between 0.1 mm and 1 mm.

12. The medical instrument according to claim 1, wherein the first bearing surface and/or second bearing surface have an area of between 0.5 cm² and 5 cm².

13. The medical instrument according to claim 1, wherein a roughness Ra of the first bearing surface and/or of the second bearing surface is smaller than 1 μm.

14. The medical instrument according to claim 1, wherein the first bearing portion and first bearing surface are integrally formed with the first instrument branch in a homogeneous body of unitary construction.

15. The medical instrument according to claim 1, wherein:
the first stepped portion comprises a base end and a bearing surface end,
the first shoulder portion connects the base end to the bearing surface end,
the base end has a first diameter,
the bearing surface end has a second diameter less than the first diameter, and
the first bearing surface extends on the bearing surface end.

16. The medical instrument according to claim 15, wherein the first stepped portion is frustoconical.

17. The medical instrument according to claim 15, wherein the rounded sidewall comprises a chamfer.

18. A medical instrument comprising:

a first instrument branch comprising a first bearing portion with a first bearing surface, the first bearing surface consisting of a first planar surface; and a second instrument branch comprising a second bearing portion with a second bearing surface, the second bearing surface consisting of a second planar surface, the first bearing surface resting on the second bearing surface in a pivot-sliding manner, so that the first instrument branch is pivotable about a pivot axis relative to the second instrument branch, the first bearing surface and the second bearing surface forming an interface where the first bearing surface and the second bearing surface contact one another and slide along one another under a frictional resistance during sliding pivot movement of the first instrument branch relative to the second instrument branch, the first bearing portion comprising a first stepped portion that is surrounded by a first shoulder portion such that the first bearing surface projects from the first instrument branch, the first shoulder portion defining a rounded sidewall consisting of a continuously rounded surface devoid of inside corners or gaps, and the interface consisting of a continuous planar area devoid of any void space between the first bearing surface and the second bearing surface, the continuous planar area having a fixed boundary and a fixed orientation relative to the pivot axis that remain constant during sliding pivot movement of the first instrument branch relative to the second instrument branch, wherein the first bearing surface consists of a first circle having a first diameter and the second bearing surface consists of a second circle having a second diameter, the first diameter being equal to the second diameter.

19. The medical instrument according to claim 18, wherein the first circle and the second circle are concentric.

* * * * *